United States Patent
Kimmel

(10) Patent No.: US 11,710,132 B2
(45) Date of Patent: *Jul. 25, 2023

(54) USER CONTROLLED EVENT RECORD SYSTEM

(71) Applicant: Scott Kimmel, Boynton Beach, FL (US)

(72) Inventor: Scott Kimmel, Deerfield Beach, FL (US)

(*) Notice: Subject to any disclaimer, the term of this patent is extended or adjusted under 35 U.S.C. 154(b) by 98 days.

This patent is subject to a terminal disclaimer.

(21) Appl. No.: 17/538,342

(22) Filed: Nov. 30, 2021

(65) Prior Publication Data

US 2022/0092602 A1 Mar. 24, 2022

Related U.S. Application Data

(63) Continuation of application No. 16/537,860, filed on Aug. 12, 2019, now Pat. No. 11,210,671, which is a
(Continued)

(51) Int. Cl.
*G06F 21/32* (2013.01)
*G06Q 20/40* (2012.01)
(Continued)

(52) U.S. Cl.
CPC ......... *G06Q 20/4016* (2013.01); *G06F 21/32* (2013.01); *G06F 21/6245* (2013.01); *G06Q 20/326* (2020.05)

(58) Field of Classification Search
CPC . G06Q 20/4016; G06F 21/32; G06F 21/6245; G16H 10/60; G16H 50/30; G16H 50/20; G16H 50/70; G16H 10/20
See application file for complete search history.

(56) References Cited

U.S. PATENT DOCUMENTS 5,070,452 A 12/1991 Doyle, Jr. et al.
5,071,168 A 12/1991 Shamos
(Continued)

FOREIGN PATENT DOCUMENTS

CA 2890740 A1 5/2013
CN 104971437 A 10/2015
(Continued)

OTHER PUBLICATIONS

"Health Care Fraud a Serious and Costly Reality for All Americans," pp. 1-9. Downloaded Feb. 13, 2018.
(Continued)

*Primary Examiner* — Peter H Choi
*Assistant Examiner* — Chad A Newton
(74) *Attorney, Agent, or Firm* — Pablo Meles

(57) ABSTRACT

A user controlled mobile device for use in countering phantom billing fraud in connection with receiving or providing health care services includes one or more components capturing and outputting biometric data and location data, and a data storage device holding an event record created without explicit user intervention indicating whether the particular user was at the particular location, the event record including a timestamp corresponding to events at or near a time of the timestamp including a time of capture of the biometric and location data, the biometric data and location data, where the stored event record serves as the personal audit trail evidencing an existence or absence of phantom billing.

22 Claims, 3 Drawing Sheets

Related U.S. Application Data continuation of application No. 15/895,319, filed on Feb. 13, 2018, now Pat. No. 10,423,964.

(60) Provisional application No. 62/612,007, filed on Dec. 29, 2017.

(51) Int. Cl.
*G06F 21/62* (2013.01)
*G06Q 20/32* (2012.01)

(56) References Cited

U.S. PATENT DOCUMENTS

| | | | |
|---|---|---|---|
| 5,193,855 A | 3/1993 | Shamos | |
| 5,224,173 A | 6/1993 | Kuhns | |
| 5,359,509 A | 10/1994 | Little et al. | |
| 5,457,747 A | 10/1995 | Drexler et al. | |
| 5,566,327 A | 10/1996 | Sehr | |
| 5,845,255 A | 12/1998 | Mayaud | |
| 5,879,453 A | 3/1999 | Streeter et al. | |
| 5,884,271 A | 3/1999 | Pitroda | |
| 5,976,926 A | 3/1999 | Beecham | |
| 5,930,804 A | 7/1999 | Yu et al. | |
| 5,997,339 A | 12/1999 | Fuji et al. | |
| 6,012,035 A | 1/2000 | Freeman, Jr. et al. | |
| 6,097,035 A | 8/2000 | Belongie et al. | |
| 6,122,737 A | 9/2000 | Bjorn et al. | |
| 6,125,192 A | 9/2000 | Bjorn et al. | |
| 6,154,727 A | 11/2000 | Karp et al. | |
| 6,188,781 B1 | 2/2001 | Brownlee | |
| 6,188,871 B1 | 2/2001 | Kitamura et al. | |
| 6,208,973 B1 | 3/2001 | Boyer et al. | |
| 6,282,303 B1 | 8/2001 | Brownlee | |
| 6,282,576 B1 | 8/2001 | Lane | |
| 6,282,648 B1 | 8/2001 | Walker et al. | |
| 6,292,576 B1 | 9/2001 | Brownlee | |
| 6,394,356 B1 | 5/2002 | Zagami | |
| 6,799,275 B1 | 9/2004 | Bjorn | |
| 6,820,058 B2 | 11/2004 | Wood | |
| 6,820,059 B2 | 11/2004 | Wood | |
| 6,826,535 B2 | 11/2004 | Wood | |
| 6,826,537 B1 | 11/2004 | Wood | |
| 6,826,636 B2 | 11/2004 | Forman | |
| 6,944,566 B2 * | 9/2005 | Chen | G06F 18/25 324/614 |
| 7,058,585 B1 | 6/2006 | Wood | |
| 7,209,886 B2 | 4/2007 | Kimmel | |
| 7,421,398 B2 | 9/2008 | Kimmel | |
| 7,421,399 B2 | 9/2008 | Kimmel | |
| 7,464,040 B2 | 12/2008 | Joao | |
| 7,769,207 B2 | 8/2010 | Olivo, Jr. | |
| 7,817,844 B2 | 10/2010 | Kitamura et al. | |
| 7,890,752 B2 | 2/2011 | Bardsley et al. | |
| 8,028,896 B2 | 10/2011 | Carter et al. | |
| 8,126,738 B2 | 2/2012 | Green et al. | |
| 8,126,739 B2 | 2/2012 | Green et al. | |
| 8,200,708 B2 | 6/2012 | Ghosh et al. | |
| 8,320,638 B2 | 11/2012 | Pitt | |
| 8,392,210 B2 | 3/2013 | Beraja | |
| 8,392,211 B2 | 3/2013 | Beraja | |
| 8,392,212 B2 | 3/2013 | Beraja | |
| 8,392,213 B2 | 3/2013 | Beraja | |
| 8,396,282 B1 * | 3/2013 | Huber | G06F 18/253 382/153 |
| 8,438,182 B2 | 5/2013 | Gillam et al. | |
| 8,457,595 B2 | 6/2013 | MacInnis et al. | |
| 8,583,454 B2 | 11/2013 | Beraja | |
| 8,751,264 B2 | 6/2014 | Beraja et al. | |
| 8,799,010 B2 * | 8/2014 | Kaundinya | G06Q 10/10 705/2 |
| 8,818,825 B1 | 8/2014 | Scorvo | |
| 8,862,486 B2 | 10/2014 | Cordova et al. | |
| 9,098,852 B1 | 8/2015 | Dangott et al. | |
| 9,215,979 B2 | 12/2015 | Brown | |
| 9,495,465 B2 | 11/2016 | Bowers et al. | |
| 9,515,836 B2 | 12/2016 | Tredoux et al. | |
| 9,530,137 B2 | 12/2016 | Weiss | |
| 9,633,396 B2 | 4/2017 | Hill | |
| 9,703,931 B2 | 7/2017 | Hinkel | |
| 9,740,823 B2 | 8/2017 | Breazeale, Jr. | |
| 9,876,803 B2 | 1/2018 | Miu et al. | |
| 11,210,671 B2 * | 12/2021 | Kimmel | G06F 21/6245 |
| 2002/0030584 A1 | 3/2002 | Perler | |
| 2002/0054695 A1 | 5/2002 | Bjorn | |
| 2002/0133725 A1 | 9/2002 | Roy | |
| 2002/0138306 A1 | 9/2002 | Sabovich | |
| 2002/0188467 A1 | 12/2002 | Eke | |
| 2003/0093298 A1 | 5/2003 | Hernandez | |
| 2004/0143454 A1 * | 7/2004 | Kimmel | G06Q 10/10 705/2 |
| 2005/0125258 A1 | 6/2005 | Yellin | |
| 2009/0313049 A1 * | 12/2009 | Joao | G16Z 99/00 707/999.009 |
| 2010/0274583 A1 * | 10/2010 | Beraja | H04W 4/02 342/357.34 |
| 2011/0189980 A1 * | 8/2011 | Proulx | G06F 16/48 455/414.1 |
| 2011/0209214 A1 * | 8/2011 | Simske | G06F 21/73 726/21 |
| 2012/0095779 A1 * | 4/2012 | Wengrovitz | G16H 10/60 705/3 |
| 2014/0004828 A1 * | 1/2014 | Han | H04W 64/00 455/411 |
| 2014/0016835 A1 * | 1/2014 | Song | G10L 17/06 382/118 |
| 2015/0227697 A1 * | 8/2015 | Nelson | G16B 50/00 705/3 |
| 2017/0097413 A1 * | 4/2017 | Gillian | A63F 13/24 |

FOREIGN PATENT DOCUMENTS

| | | |
|---|---|---|
| GB | 201316565 | 10/2013 |
| WO | WO2002025528 A1 | 3/2002 |
| WO | WO2004049128 A3 | 6/2004 |
| WO | WO2004049129 A2 | 6/2004 |

OTHER PUBLICATIONS

Lisa M. Jackson, "Efforts to Combat Health Care Fraud: A Study of NYSE Listed Health Care Service Companies," pp. 1-29.

Smart Card Alliance, Smart Card Applications in the U.S. Healthcare Industry, Feb. 2006, pp. 1-36.

Malcolm K. Sparrow, "Controlling Fraud and Abuse in Medicaid: Innovations and Obstacles," A Report from the "Executive Seminars on Fraud and Abuse in Medicaid," Sep. 24, 1999 pp. 1-51.

* cited by examiner

USER CONTROLLED EVENT RECORD SYSTEM

CROSS-REFERENCE TO RELATED APPLICATIONS

This application is a continuation application of U.S. application Ser. No. 16/537,860 filed Aug. 12, 2019 which is a continuation of U.S. application Ser. No. 15/895,319 filed Feb. 13, 2018 which claims priority under 35 U.S.C. Section 119(e) to U.S. Provisional Application No. 62/612,007, filed Dec. 29, 2017, the entire contents of the aforementioned applications are incorporated herein by reference thereto.

FIELD OF THE DESCRIPTION

The present invention relates, in general, to methods and systems for enabling mobile device users to create, manage and authorize access to event records, and more particularly, to methods and systems that use mobile device sensors to create event records that can be used to detect and prevent fraudulent transactions including healthcare fraud.

RELEVANT BACKGROUND

There is growing interest in location-based services in diverse fields such as recreation, entertainment, health care and transaction processing. This interest arises in part because of the wide availability of mobile devices (e.g., smart phones, tablets, laptop computers and the like) with components that provide increasingly accurate location information using several information sources such as GPS, WIFI, Bluetooth®, near field communication (NFC), image analysis and the like.

At the same time, driven by personalization and security desires, mobile devices include components for capturing and using various biometrics. Components include fingerprint readers, facial recognition, iris recognition, voice recognition and the like. Biometric information may be used locally on the mobile device, but is often communicated to remote third party services for analysis and storage.

While users appreciate the functionality provided by these location and biometric components, the information captured is largely out of the user's control. Cell service provider records may contain location tracking records that are inaccessible to the user. Captured biometric data such as face images, fingerprint scans and voice samples may be stored in remote servers unbeknownst to users. As a result, the information has the potential to be used by third parties in ways that conflict with user expectations and desires.

For instance, some hospitals employ fingerprint scanners for patient registration which allows access to their electronic health record. The patient is unaware that their health record may be used by data mining companies to make health care decisions on their behalf which may not be accurate. As an example, a person who has a family history of diabetes may be placed on preventative medicine resulting in adverse consequences even though diabetes may never manifest in this person.

There is continuous and growing tension between the usefulness of these technical advancements and concerns over unwanted surveillance. People perceive a requirement to submit personal information as intrusive surveillance when it is required by a third party, but accept it willingly when personal information is under their own control and they can easily choose how the data is used. Nowhere is this tension more prevalent than in the field of medical services where the patient wants to be in control of their own health records and determine access by a third party for themself. Medical services involve numerous providers (e.g., physicians, nurses, technicians and the like), facilities (e.g., hospitals, laboratories, and the like) as well as private insurance companies, Medicare or other payer entities. Efforts to prevent fraud using technical advancements such as biometric and location information have been proposed, but are resisted at various levels because providers and to a lesser extent insurance companies lack sufficient incentive to install systems to routinely gather and use biometric and location information to prevent fraud. Moreover, solutions that involve using this type of information often involve government legislation and regulation which may be difficult and costly to achieve.

A related issue involves health care records, or other sensitive records. By some estimates, one in three Americans have had their health care records lost or stolen through data breaches and hacks. In June 2015 nearly 22 million federal employees suffered employment records compromised by a data breach of the Office of Personnel Management. These breaches may enable hackers and thieves to impersonate victims using data from the compromised records. These impersonations are difficult to detect since the thieves possess the same credentials (such as social security numbers, home addresses, etc.) that the victims must continue using in their day-to-day lives. Victims of such crimes need better ways to detect and repudiate fraudulent uses of their stolen personal information.

In particular, U.S. Pat. Nos. 7,209,886; 7,421,398 and 7,421,399 entitled "System and Method for Implementing Healthcare Fraud Countermeasures" which are incorporated herein by reference in their entirety, describe solutions to the persistent problem of phantom billing in which providers bill insurance companies for services that are not in fact rendered. These patents describe a relatively simple solution that uses biometric and location information to allow providers to create an event record that proves a patient is present when services are provided, thereby eliminating the risk of phantom billing. However, this system requires providers to install and use hardware and software which adds expense with little perceived improvement in efficiency or profitability to their practice. In the case of providers who commit phantom billing fraud, the resistance is because they would be caught. While insurance companies recognize the benefits of preventing phantom billing, so long as they can pass the cost of phantom billing onto the insured they lack sufficient incentive to require these tools. As a result, it is the insured patients that pay the cost of phantom billing and until now they have been relatively powerless because it is all the other industry participants that gather and control the data necessary to prevent phantom billing.

The growing tension exists in part because individuals are not in control of the data that is being gathered. Users are often faced with a take it or leave it choice to allow a mobile app or service to use biometric and location information, or simply not use the mobile app. A need exists for systems and methods that enable user control over location and biometric data that facilitate usage of the data by third party services, but retain fine grained user control over when, why and how that data is used.

SUMMARY

Briefly stated, a specific implementation of the present invention involves a system that enables patients to actively participate in fraud prevention using information gathered on a mobile device such as a smart phone. Patient mobile devices capture location information using one or more components of the mobile device including but not limited to GPS, assisted GPS, WIFI, Bluetooth, near field communication, image analysis, audio processing, magnetometers, and accelerometers. Patient mobile devices capture biometric information using one or more components of the mobile device including fingerprint readers, image analysis, voice processing, temperature sensors magnetometers and accelerometers. The location information and biometric information and time of capture are associated in an event record together with a timestamp and any other desired data relevant to events occurring or detected at or near the time of the timestamp. The event record is stored in a cryptographically secure data store that can be unlocked with a key known to the patient such as a password, biometric, keycard, pin number, certificate or any key technology with sufficient security characteristics for a particular application. The data store may be implemented on the user device or on a remote server or cloud-based data storage. A patient interface enables the patient to specify access permissions for individual event records where the access permissions grant third party services and applications permission to read the specified event record(s) from the cryptographically secure data store. To prevent or detect billing fraud, a patient grants permission to a third-party payer to read one or more event records corresponding to a time and/or place at which health care services were allegedly provided. The event record confirms the patient was (or was not) present at a location where health care services were provided at the time services were provided and the insurer may process the payment accordingly.

More generally, the present invention involves a system for creating, managing and granting access permissions to event records for any purpose desired by a user. A mobile device captures location information using one or more components of the mobile device including but not limited to GPS, assisted GPS, WIFI, Bluetooth, near field communication, image analysis, audio processing, magnetometers, and accelerometers. The mobile device captures biometric information using one or more components of the mobile device including fingerprint readers, image analysis, voice processing, temperature sensors magnetometers and accelerometers. The location information and biometric information and time of capture are associated in an event record together with a timestamp and any other desired data relevant to events occurring or detected at or near the time of the timestamp. The event record is stored in a cryptographically secure data store that can be unlocked with a key known to the patient. The data store may be implemented on the user device or on a remote server or cloud-based data storage. A user interface enables the user to specify access permissions for individual event records where the access permissions grant third party services and applications permission to read the specified event record(s) from the cryptographically secure data store. Either upon request or at the user's initiative the user specifies access permissions to the secure data store enabling third party services, apps or applications to access specified event records to provide desired services.

DETAILED DESCRIPTION

The innovations and improvements described herein are presented in terms of specific implementations that address fraud detection and prevention, particularly phantom billing fraud (i.e., billing for a patient who is not physically present to receive services), in the healthcare industry. More generally, however, the techniques and systems described herein implement new ways for individuals to interact with and control data about themselves, their comings and goings, and their day-to-day interactions with businesses, governments and each other. For too long the technical advancements that have collected data about individual's day-to-day events have been controlled by third parties rather than the individuals themselves resulting in mistrust and lost utility.

Figure 1A:
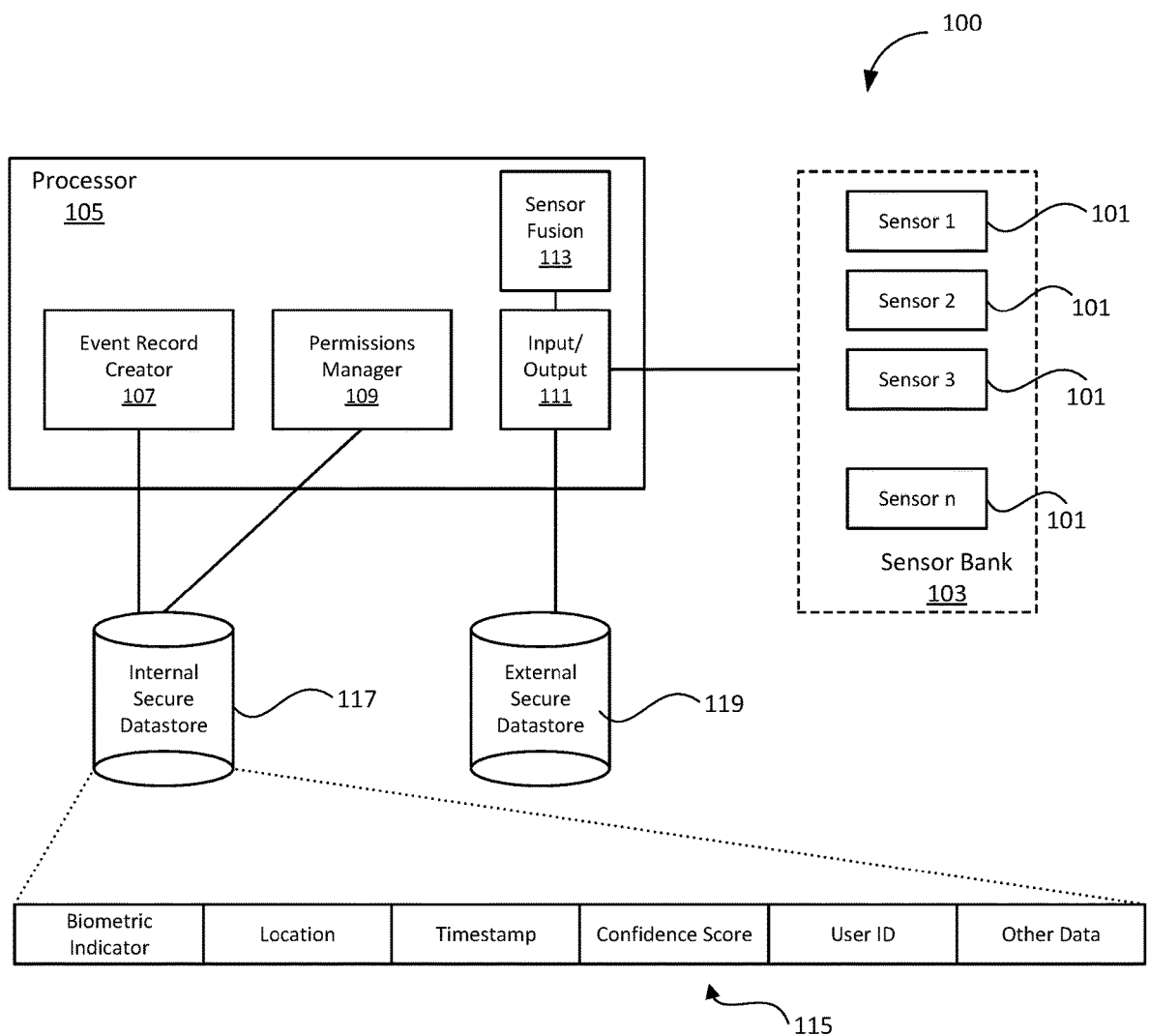
FIG. 1A is functional block drawing of a system implementing a mobile device in accordance with the present invention.

Referring first to the more general implementations, FIG. 1A illustrates a mobile device 100 configured to implement features of the present invention. Mobile device 100 may be a special-purpose device having the components described herein, or more preferably is implemented in a commercially available smartphone. Commercially available tablet computers, phablets, and laptop computers may also be suitable platforms for implementation of mobile device 100 so long as the device has ability to determine its location, ability to obtain biometric information about a user, and ability to create and store event records described herein. As smartphones and other mobile computing devices exist and continue to evolve, they have multiple sensors 101 such as image devices and cameras, fingerprint scanners, temperature sensors, accelerometers, microphones, pulse rate sensors and the like. They also implement sensors that more specifically function as location sensors such as GPS, WIFI, Bluetooth® and near field communication (NFC). Theses sensors are typically implemented for specific purposes other than implementing the biometric and location functions of the present invention, but in accordance with the present teachings the data they produce can be captured and used to implement the systems disclosed herein.

For convenience, sensors 101 are logically grouped in sensor bank 103 in FIG. 1 and in the description herein, however, they typically are implemented as separate subsystems of a mobile device and are not electrically or functionally connected. In any given situation some sensors 101 may be operable and others inoperable or inaccurate. Given the flexibility with which electronic devices can be implemented, the components shown in FIG. 1, including sensors 101 and sensor bank 103 can be integrated into a single device, or alternatively implemented in two or more separate devices that communicate with each other. For example, a sensor 101 that acts to detect pulse rate may be implemented as a wearable wristband that communicates with a smartphone.

Processor 105 implements various software, hardware and firmware components such as event record creator 107, permissions manager 109, input/output services 111 and sensor fusion services 113. Processor 105 may be implemented as a single microprocessor or microcontroller or more typically is a system on a chip (SoC) with closely coupled components that integrates one or more processors, memory, management logic as well as other components of a computer or other electronic system such as a smartphone. Processor 105 may contain digital, analog, mixed-signal, and often radio-frequency functions implemented on a single substrate.

Processor 105 implements processes to create, store and manage event records 115. Event record 115 comprises data that documents basic information about an event such as where the event occurred (location), who was present (biometric indicator), time the event occurred (timestamp) as well as optional data such as confidence score(s) related to the biometric indicator and location information. Event record 115 may also contain a user ID which is a unique identification of the user (such as a patient or member ID used by an insurance company). Explicit inclusion of the user ID within event record 115 may not be required in some instances because the mobile device 100 implicitly identifies the user with its unique phone number or IMEI number or the like when either of those identifications are uniquely associated with a specific user. Moreover, the biometric indicator within event records 115 may sufficiently identify the user such that the event record 115 can be readily associated with a unique user by matching the biometric indicator against references. However, including a user ID within the event records 115 may have practical benefits in avoiding additional processing to lookup a specific user based on biometric, phone number, IMEI or the like. Additionally, event record 115 may store other data about the event such as familiar names of places (e.g., a hospital name or a store name) or other people (e.g., Dr. Jones, or a sales clerk identification), that are relevant to a particular event. In a general sense an event is documented by who, where, and when information and the other data optionally added to an event record conveniently customizes the event record for a variety of uses.

A first important capability implemented by processor 105 is to form and securely store event records 115 in a user-controlled data storage such as internal secure datastore 117 or external secure datastore 119. Forming event records 115 may comprise concatenation of the various data components described above into a suitably formed record, or may involve creating relationship links between separate data components. The decision of how to implement secure data storage 117/119 is a matter of selecting database storage functionality to provide the accessibility and reliability necessary for a particular application. Security of datastore 117/119 is important in many applications because of the highly valuable information provided by a collection of event records 115 that document events of a personal nature in great detail. In particular implementations the datastores 117/119 may be cryptographically protected by biometric information such as fingerprints, iris prints, voice prints or the like, or more preferably by passwords/passcodes that are known to the user.

Permissions manager 109 enables a user to specify access permissions and access conditions to individual event records 115 or groups of event records 115. These specified permissions enable third party requests for event records to be satisfied according to user-specified conditions. Permissions manager 109 may implement a user interface enabling a user to specify access permissions and access conditions that are relevant to a particular application. Permissions manager 109 may also implement a rules engine that tests access requests to see if they satisfy the user-specified permissions and conditions as a part of enabling access to event records 115. Access permissions, for example, may comprise very restrictive access that requires the requestor to present a digital certificate proving their identity for particular third party event record request that are perceived as requiring high security by the user (e.g., requests from a financial institution or government entity). At the same time, liberal access permissions requiring no certified identity may be granted to trusted third party event record requests, such as those generated by a third party fitness tracker app that executes locally on the user's mobile device 101. This may seem counterintuitive that an app implementing functions of seemingly lower importance would be granted more permissive access than a high security function, but one advantage of the present invention is an ability to implement these seemingly counterintuitive permissions based on the user's own perception of needed security.

Users may also specify access conditions in a manner similar to permissions. Access conditions are very similar to access permissions and may be implemented by the same hardware and software processes. Alternatively they may be implemented by distinct processes. Whereas access permissions relate qualitatively to who the request is coming from, access conditions relate to when the request is received, how the requested information will be used, where the request is inquiring about or other event criteria that the user desires to exercise control over access to event records 115. For example, a user may specify a condition that states an insurance company may access event records around a narrow window of time surrounding a health care appointment or meeting, but have no access to event records during times that do not satisfy the user specified conditions. Similarly, conditions may specify locations such that event records 115 corresponding to particular locations are accessible, but event records corresponding to locations that do not satisfy the user-specified conditions are not accessible. As another example, a user-specified condition may require the access request to identify how the access request will be used (e.g., the request will be used for payment purposes, but it will not be used for marketing purposes). Permissions manager 109 examines the request and tests the request against user-specified permissions and user-specified conditions, and grants access to event records 115 when the permissions and conditions are satisfied.

Third party requests may come from remote third party entities such as an insurance carrier, government agency or bank submitting request messages via input output services 111, or may come from applications running on mobile device 100 such as a personal time and attendance program or fitness tracker. Third party requests from remote services may be addressed to a particular user's mobile device 100 using an addressing technique appropriate for the particular message protocol. For example, a request may be sent using email or simple message services (SMS) text using an email address or phone number associated with the particular user respectively. Push notifications to a mobile device may also be used as can proprietary message protocols. In the case of third party applications implemented on the mobile device itself messages can be sent using operating system resources in a manner conventional for the particular operating system on mobile device 100. Permissions may be specified in advance, or may be specified in response to received third party requests. For example, if an employer wished to verify that an employee were present at a conference, the employer could send a request for event records corresponding to a time of the event, or a place of the event. Permissions manager 119 reviews or requests user-specified permissions and may grant or deny access to corresponding event records 115.

Preferably permissions are maintained on a record-by-record basis as any given event records 115 has multiple potential uses and may treat third party requests differently. For example, a user may permit access to an insurance provider for records created during a narrow time window around a scheduled appointment, but allow a trusted fitness tracker application running on mobile device 100 access multiple event records 115 to compute events such as walking or gym visits. In this manner, the user's own assessment and trust of the requesting entity is paramount in determining whether or not event records 115 are made available.

A first important capability of sensor bank 103 is to capture biometric data. As used herein, biometric data refers very generally to any data that is unique to a person operating mobile device 100. This includes explicit traditional biometric information such as fingerprint data provided by a sensor 101 implemented as a fingerprint scanner. This also includes less traditional data sources such as facial data captured by an image sensor, voice data captured by a microphone, gait data captured by an accelerometer and the like.

A second important capability of sensor bank 103 is to capture location data. As used herein, location data refers very generally to any data that is unique to a location mobile device 100. This includes explicit traditional location information such as GPS data or WIFI assisted GPS data provided by one or more sensors 101. This also includes less traditional data sources such as image data captured by an image sensor, acoustic data captured by a microphone, motion data captured by an accelerometer, magnetic field data captured by a magnetometer and the like.

One feature of the present invention is that the data captured from sensors 101 can be used directly, or further processed by components in processor 105 such as sensor fusion component 113 using sensor fusion algorithms to increase confidence of captured biometric information and/or location information. Exemplary confidence fusion techniques are described in the article by M. Siegel and Huadong Wu, "Confidence fusion [sensor fusion]," International Workshop on Robot Sensing, 2004. ROSE 2004, 2004, pp. 94-99 which is incorporated herein by reference. Data from sensors 101 is captured by processor 105 via input/output component 111. Input/output component 111 implements analog and/or digital interface electronics suitable to couple to each sensor 101 and capture the signals produced. Sensor fusion component 113 couples to input/output component 111 and operates to condition data from sensors 101, determine confidence levels associated with data from individual sensors 101, and to determine composite location and biometric information based on data from one or more sensors 101. This serves both to reduce the amount of user involvement in data capture as well as to improve the accuracy and reliability of the biometric information. This feature also compensates for situations in which particular sensors 101 do not operate well, such as GPS sensors inside a building.

Another feature of the present invention is that sensor fusion techniques may be used over a period of time to increase confidence. For example, while a GPS signal may be unavailable inside a hospital, a reliable GPS signal may have been available minutes before entering the hospital. Other sensors 101 may reliably detect acceleration of an elevator inside the hospital, or WIFI signals within the hospital, or an image of the hospital interior or health care personnel, and while by themselves insufficient to pinpoint location, the data from all sources may be combined or fused to reliably indicate location within the hospital even though the various data components arrived at slightly different times. One way of combining this information is to determine confidence level of each sensor input based on factors such as signal strength, uniqueness, etc., weight these individual confidences and add them to determine a composite confidence of location. Similar techniques can be used to determine a composite confidence level for biometric information from multiple sensors 101. For example, marginal fingerprint data due to a variety of reasons is augmented with an image capture of the user's face and/or voice recognition from data captured by a microphone, weighted by individual confidence level determinations, and added or otherwise algorithmically combined to form a composite confidence level.

Figure 1B:
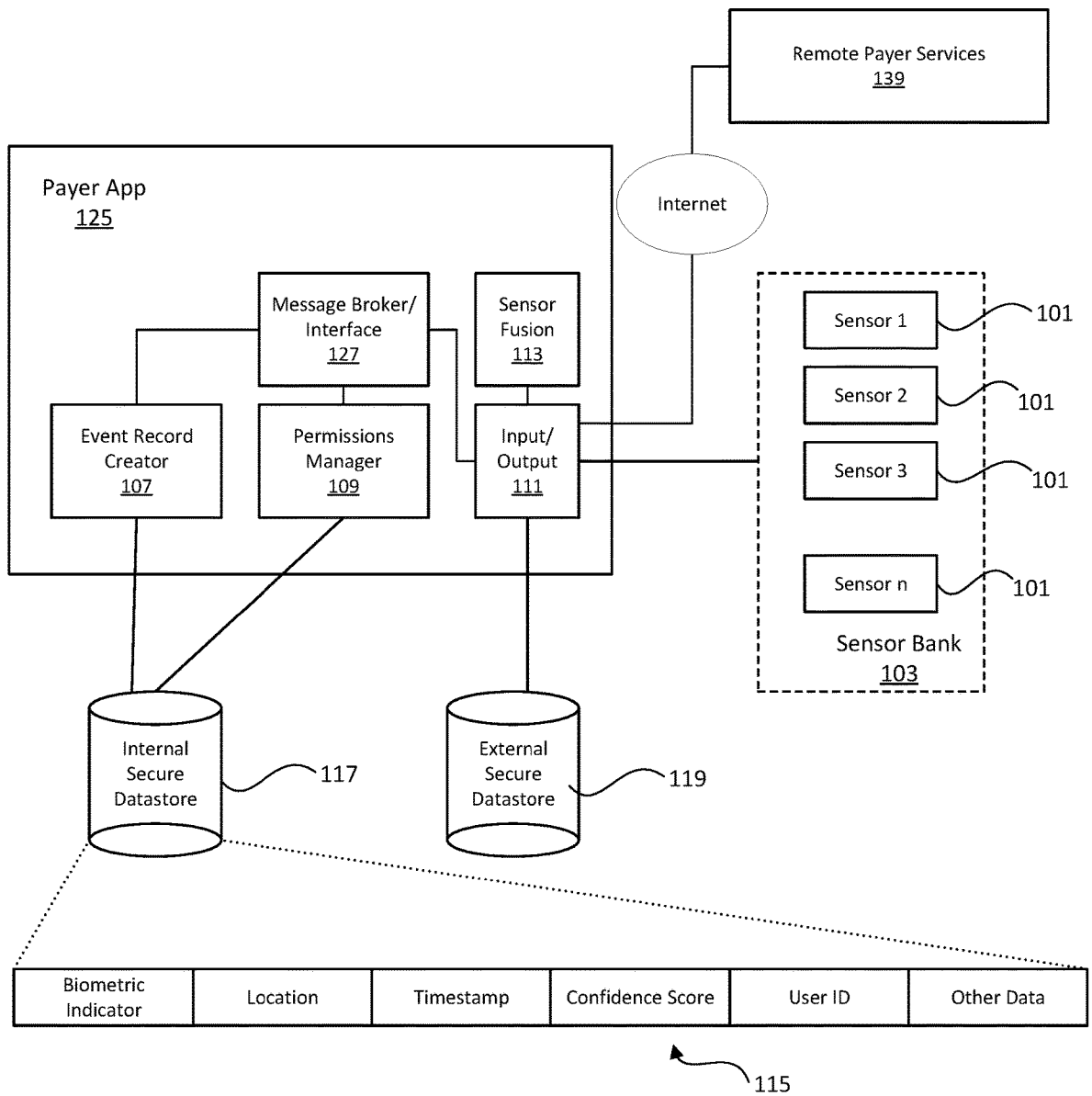
FIG. 1B is a functional block diagram of an alternative embodiment in accordance with the present invention.

FIG. 1B illustrates a variation on the system described in FIG. 1A that may have commercial advantages in some implementations. Components shown in FIG. 1B that are identified with similar numbers are implemented and perform similar functions as described in reference to FIG. 1A and will be minimally described in reference to FIG. 1B. The implementation of FIG. 1A implements processes 107, 109, 111 and 113 in a manner that is agnostic to third party services (e.g., a third party payer service) and so manages event records 115 in a way that makes them available to a variety of third party services as the user permits. In contrast, the implementation of FIG. 1B implements a payer app 125 which may execute on a mobile processor 105, but implements processes for event record creator 127, permissions manager 129, input output services 131 and sensor fusion service 133 as a part of a dedicated app that is associated with a particular remote payer service 139.

As a specific example, an insurance company or government agency may implement remote payer services 139 in a brand-specific manner for a single insurance company, or as an alliance of several insurance companies. In the implementation of FIG. 1B, event records 115 remain accessible by user permissions, but only to remote payer services 139. In operation, remote payer services 139 generates an event record request message over, for example, an internet connection, to input output services 131 of payer app 125. The request message may be generated in response to a request for payment received from a health care provider, for example. Alternatively, the request message may be triggered periodically or by any other event that is appropriate for a particular application. The request message contains sufficient information to identify event records 115 of interest such as time of service, location, health care provider ID, and the like.

The request message is handled by message broker/interface 127 which preferably implements an authentication protocol to authenticate that the event record request has in fact come from a known remote payer service 139. This optional step creates a barrier to hacking and can provide the user with a higher level of confidence in the security of event records 115. Message broker/interface 127 parses the request message and accesses permissions manager 129 to determine whether the user has granted sufficient permissions to respond to the request. When insufficient permissions have been granted, message broker/interface 127 generates a response message back to remote payer services 129 indicated the request was unsuccessful. When sufficient permissions have been granted, message broker/interface 127 generates a response indicating success to remote payer services 129. The success response may include the responsive event records 115, or in many cases summary information from the responsive event records 115, or simply a binary indication that the requested event records exist.

In other cases message broker/interface 127 may operate without a request message from remote payer services 129.

Because payer app 125 is associated with a specific remote payer service, it may be pre-programmed to generate event record "push" message based on internal triggers rather than external requests. For example, message broker/interface 127 may periodically or from time to time query datastores 117/119 for event records that have been created over a particular time period and push those records to remote payer service 129. These push records may include event records 115, or in many cases summary information from the responsive event records 115, or simply a binary indication that the requested event records exist.

In the implementation of FIG. 1B event records 115 may be created continuously as described in reference to FIG. 1A, or they may be created on demand in response to a request from remote payer services 129, or in response to a request from a user. For example, when a patient arrives at an appointment for health care services they may open their health care payer app 125 to accomplish some task such as providing their insurance information to the health care provider or authenticating themselves to the health care provider and providing evidence that they are covered by particular insurance. At that time the provider app 125 may ask the user to turn on event record creator service 127, or that service may activate automatically for a period of time.

Figure 2:
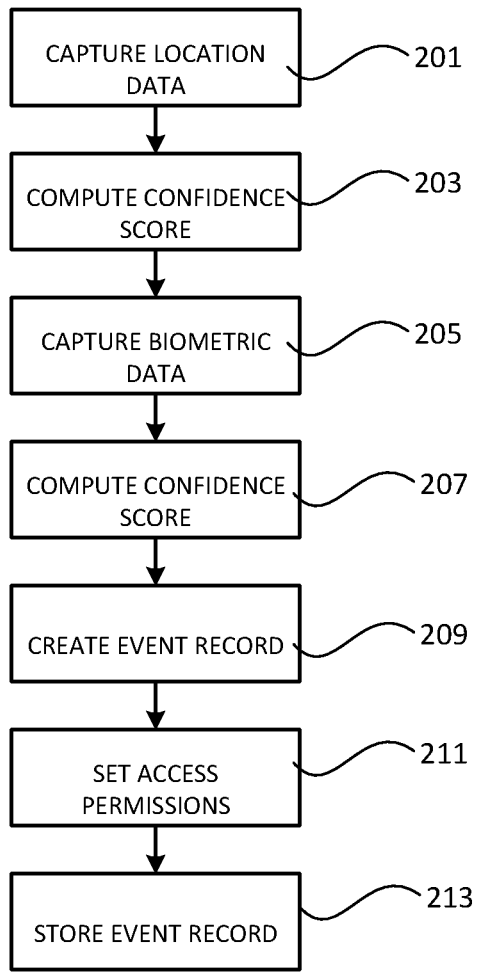
FIG. 2 is a flow diagram of processes for capturing event records.

FIG. 2 illustrates processes involved in an exemplary operation of capturing, storing and managing event records 115. The processes shown in FIG. 2 may be performed in any order unless specified otherwise herein, and may run continuously, periodically or on demand to satisfy user preferences and needs of a particular application.

In operation 201 location data is captured, for example, by accessing appropriate sensors 101. Location data may be in suitable format as received by input/output services 111 such as when a reliable GPS sensor 101 provides latitude and longitude information. Alternatively or in addition, raw data from sensors 101 may require conditioning or processing to determine location with suitable confidence. For example, an image of a building exterior or interior may require image processing to lookup a location corresponding to the image. Audio data may require processing to identify unique audio signatures of a location. In these later instances data processing functions within sensor fusion component 113 or implemented separately by processor 105 process the raw sensor data to determine location information.

Preferably, a confidence score for the location data is computed in operation 203. Some sensors 101 provide confidence indicators explicitly, while others may provide confidence implicitly in that they do not provide any data when confidence is below determined thresholds. In yet other cases confidence indicators may not be provided at all such as when image or audio data is used. In operation 203 confidence scores are determined and/or computed to indicate the reliability and accuracy of particular location data. Because different third party applications may have different confidence requirements it is desirable to continue processes 201 and 203 iteratively until a suitable level of confidence is obtained. Alternatively or in addition, confidence indicators may be implemented by specifying some attribute of the sensor(s) 101 from which the location data is obtained. For example, indicating that location data was obtained from a GPS device implies a level of accuracy and reliability such that actual scoring need not be performed because simply knowing that the location data was sourced from a GPS device will suffice. In contrast, indicating that the location data came from an image sensor would perhaps imply lower confidence.

In operation 205 biometric data is captured, for example, by accessing appropriate sensors 101. Biometric data may be in suitable format as received by input/output services 111 such as when a fingerprint scanner or iris scanner provides minutia data reflecting the biometric itself. Alternatively or in addition, raw data from sensors 101 may require conditioning or processing to determine biometric with suitable confidence. For example, an image of a face may require image processing to lookup an individual corresponding to the image. Audio data may require processing to identify unique voice print for an individual. In these later instances data processing functions within sensor fusion component 113 or implemented separately by processor 105 process the raw sensor data to determine location information. This processing may be implemented by hardware and/or software processes implemented in mobile device 100, or alternatively may be performed by remote services.

Similar to operation 203, a confidence score for the biometric data is computed in operation 207. Some sensors 101 provide confidence indicators explicitly, such as a fingerprint scanner, while others may provide confidence implicitly in that they do not provide any data when confidence is below determined thresholds. In yet other cases confidence indicators may not be provided at all such as when image or audio data is used. In operation 207 confidence scores are determined and/or computed to indicate the reliability and accuracy of particular biometric data. Because different third party applications may have different confidence requirements it is desirable to continue processes 205 and 207 iteratively until a suitable level of confidence is obtained. Alternatively or in addition, confidence indicators may be implemented in operation 205 by specifying some attribute of the sensor(s) 101 from which the biometric data is obtained. For example, indicating that biometric data was obtained from a fingerprint device implies a level of accuracy and reliability such that actual scoring need not be performed because simply knowing that the location data was sourced from a GPS device will suffice. In contrast, indicating that the biometric data came from an image sensor would perhaps imply lower confidence.

In operation 209 an event record 115 (shown in FIG. 1) is created. Either or both of the biometric indicator and the location information may be precise (i.e., contain actual captured biometric sensor minutia or location latitude/longitude) or may be imprecise (i.e., contain a less specific indicator such as user ID or street address of a location). In some instances the biometric indicator may be a binary conclusion indicating that "yes, biometric information for the registered user was captured" rather than include the minutia itself. Likewise, location data may be represented in a conclusory fashion indicating "yes, mobile device 100 was at a specified location rather than containing GPS coordinates. Reducing event record 115 to conclusory information will reduce the general applicability of event records 115, but is a suitable alternative in some implementations such as fraud detection and prevention described below. In operation 209 the event record may include one or more confidence score(s) when determined in operations 203 and 205. The confidence score may be simplified or reduced to simply information about characteristics of the sensors 101 that have provided the data where those characteristics are relevant to a determination of confidence in the accuracy or trustworthiness of the location data and/or biometric data.

In optional step 211 the user sets access permissions for event records 115. This is optionally performed in advance of creating event records, or may be postponed entirely until an access request is received. Typical access permissions may identify a particular third party to whom access permission is granted, a time frame for which access is granted, or other conditions of approval specified by the user.

In operation 213 event records are stored locally and/or on external data storage. Preferably event records 115 are stored in a cryptographically secure manner using biometric access protocols or more preferably password or passphrase access. Any available encryption techniques and software may be used to meet the needs of a particular application.

Figure 3:
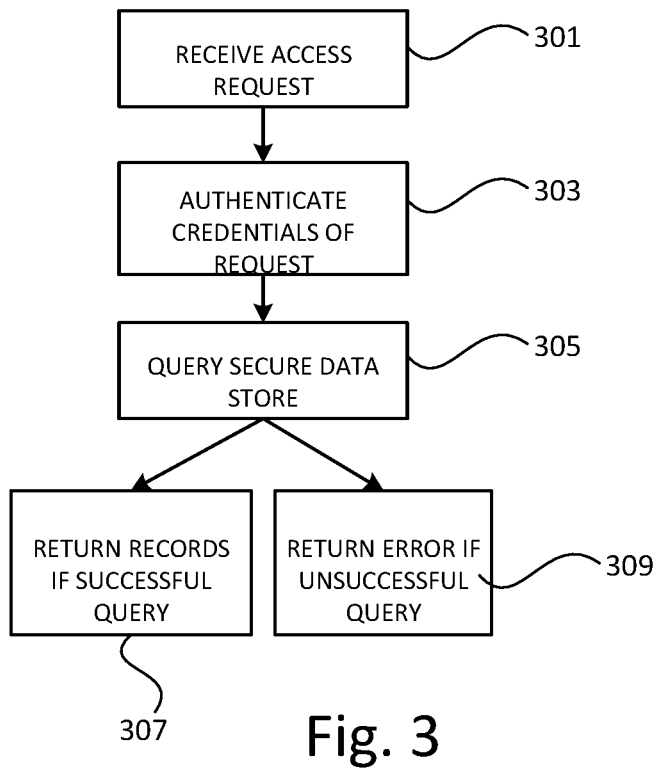
FIG. 3 is a flow diagram of processes for authorizing access to event records.

In FIG. 3, an exemplary set of operations for granting access to third parties is illustrated. In operation 301 an access request is received. Typically access requests will occur at some time after records are stored. The access request preferably is submitted with credentials to verify the requestor identity which is verified in operation 303. The access request will also contain query data that provides sufficient information to identify the particular event records 115 that are requested. This may be a particular time or range of time, or may be a particular location, or both. In operation 305 the provided query information is used to query the secure datastore 117/119 to retrieve the identified event record(s) 115. Query processes 305 also determine if the requesting user, as verified in operation 303, has been granted permissions to access the particular requested records. If access permissions have not been previously granted the system may initiate an interaction with the user to obtain necessary permission to release the records.

When records are found, and suitable user permissions have been obtained, a success message is generated in operation 307. The success message may contain the entire event record(s) 115, biometric and location data itself, or may contain summary or conclusory data only that confirms the desired records exist. In this manner the user is once again enabled to control the amount of personal data that is shared with third party applications. On the other hand, when the query is unsuccessful a message is returned in operation 309 that indicates and error or unsuccessful query. The message returned in 309 may provide information about the reason for an unsuccessful query such as no query satisfying records exist, or insufficient permissions have been granted, which may direct further activity by the entity receiving the unsuccessful response message. In one example, an indication that there are no records 115 indicating that a user was at a health care provider's location at the time of a received claim may cause the recipient to contact the user to request some other documentation, or investigate whether phantom billing exists. In another example, when a stolen credit card has been used, a message returned in step 309 indicating that no event records exist placing the legitimate card holder at a location corresponding to a received charge could be used to pro-actively detect fraud even before the card holder knows the card is lost.

Use Case: Phantom Billing Fraud.

Center for Medicare/Medicaid Services CMS's (Medicare) web site states the most common types of fraud involve doctors, dentists, clinics and other health care providers billing for services never performed or rendered. The term "never performed" or "never rendered" has been mistakenly cast as an umbrella over two very distinct type of frauds; 1) when the patient is physically present but the provider claims to perform services which were never administered and 2) when a patient is never present to receive the alleged services. The second type of fraud, when the patient is not present, is referred to as "phantom billing fraud" and represent a unique type of fraud that cannot be adequately addressed by conventional fraud prevention techniques.

While many payers have implemented "predictive analytics" software and "data mining" to identify providers who fraudulently attempt to perpetrate the first type of fraud, these are useless when it comes to proving if the patient even showed up for a visit, which is accomplished by the event record provided by the present invention to prevent the second type of fraud referred to as phantom billing. These techniques simply chase the fraud after it occurs, but do nothing to prevent fraud before it occurs. According to one of the largest clearinghouses in the United States, which processes in excess of 5 billion transactions each year, 39% of fraud perpetrated by providers is billing for a non-existent patient or phantom billing. This equates to approximately 50 billion dollars in phantom claims. The cost for this fraud is passed down to taxpayers, insured patients, and insurance company shareholders all of whom currently lack adequate tools to prevent the fraud. The present invention eliminates phantom billing by employing the solution described below.

Upon or prior to entering a medical facility for treatment, the user accesses a payer app 125 or a suitable alternative on their smart phone or mobile device. For instance, a Blue Cross insured will open a Blue Cross-provided application that executes on processor 105 and that application will implement some or all of the processes attributed to processor 105 and described in reference to FIG. 1B. Alternatively, services 107, 109, 111 and 113 may be implemented by software that is independent of the payer app (e.g., processes running on processor 105 as shown in FIG. 1A), and the payer app 125 may simply implement user interface services to gather data from a patient about a healthcare visit or claim, and messaging services to request event records from secured datastores 117/119 and forward responses to those requests to the third party payer on behalf of the patent. Hybrid implementations are also contemplated where the some or all of the services described in association with components 107, 109, 111 and 113 are implemented in both a payer app and as services that are independent of a particular payer app.

The patient may use a biometric tool at the point of service to create an event record 115 using either an application downloaded to the mobile device 100 or the mobile device 100's built in biometric sensors and background processes. Alternatively, background services implemented on mobile device 100 may capture biometric and location information and create an event record without explicit user intervention. The smartphone's location data along with a timestamp will be stored in combination to create an "event record" of location information of the provider, a timestamp, and the biometric of the patient. This record evidences the correct patient was in fact physically present for services.

Even though the event record 115 is patient-controlled and is stored in secure datastores 117/119, the patent can establish permission such that the event record 115 can be shared with reimbursement software used by payer systems. The invention can be implemented in several ways to meet the needs of a particular situation:

1) The event record 115 can be integrated with reimbursement software used by payer systems (e.g., remote payer services 129 and payer app 125 shown in FIG. 1B).
2) Alternatively, the user grants permissions to a payer or remote payer services 129 to access the event record 115 stored in a datastore (e.g., internal secure datastore 117),
3) Alternatively, the user grants permissions to a payer to access event records stored in the cloud (e.g., external secure datastore 119).

4) Alternatively, the user may allow a payer to query their event record 115 in real time or in the future.
5) Alternatively, the user may preauthorize a payer services 129 access to event records 115, for example by prompting the user to provide sufficient permissions when payer app 125 is installed such that permissions manager 129 does not need to be invoked each time a request for access to event records is received.

Since a patient desires reimbursement there is a natural incentive for the patient to permit access to event records 115 that are requested by a payer. As described below, the present invention is also amenable to further incentivizing the patient to grant permissions because the systemic savings generated by preventing fraud provide significant value that can be shared with the patient in the form of discounts, monetary compensation, lower deductibles and co-pays and the like.

Additionally, when a healthcare provider submits a claim for reimbursement, the payer may simply send a message requesting access to particular event records 115. This message can be sent to the patient for manual handling in the form of a text message, email message or other message protocol. Alternatively the provider can send a message to the payer app 125 that is implemented on the patient's mobile device 100 and the payer app 125 will use permissions manager 109. In some instances the payer app 125 maintains the secure datastore 117/119 and can handle the query directly using permissions manager 129 to determine when user permissions allow the requested access and query secure datastore 117/119 to identify records that satisfy the request. Alternatively, the payer app 125 may generate a request to a separately implemented permissions manager 109.

The absence of an event record 115 containing the biometric indicates the patient was not physically present at the location where services were allegedly provided. In addition, event records 115 may exist for the time of the alleged service but that indicate the patient was at some other location away from the place where care was allegedly provided. In this case, the payer and law enforcement community now have a biometric audit trail of location information in control of the user to confirm the patient who was billed was in a different location when the alleged services were claimed.

While systems and methods have been attempted to eliminate phantom billing fraud, both private and public payers have faced similar obstacles with respect to the ability to implement anti-fraud solutions within a medical facility. Public payers such as Medicare and Medicaid have greater capability to instruct or demand their providers implement office tools such as software through legislation. However, by the time it is passed, most of the bad actors have absconded with ill-gotten gains and often left the region or country. Private payers market their providers as best of breed" in order to attract more members. These payers are resistant towards suggesting products for their offices that implicitly accuse the providers of fraudulent practices. The current invention removes this hurdle by removing the provider from the equation and empowers the patient with a cryptographically secured event record of their medical visit.

CMS (Medicare) has publicly advocated "Better Care, Better Health, Lower Costs". A growing body of evidence demonstrates that patients who are more actively involved in their health care experience better health outcomes and incur lower costs. As a result, many public and private health care organizations are employing strategies to better engage patients.

Payer efforts to show compliance and reduce costs have resulted in creative ways of incentivizing a patient for visiting a health care provider. For instance, a payer would rather incur expenses for a diabetic to see a podiatrist 4 times per year and spend $90.00 on foot crème than have that patient not be compliant with visits and have a $9000 toe amputation. Used in health care, upon receiving a proper event record from the user, the payer can immediately send to the patient any 'coupon" or reward for biometric confirmation of the visit at the provider. This benefits the payer by eliminating the possibility of a phantom charge while rewarding the patient for medical visits which result in a healthy population. These efforts are synergistic with the improved patent engagement and control provided by the present invention. Since the patient is in control of their event records they become an active participant not only in their own health care, but in the health care organizations' efforts to prevent fraud.

For instance, Hawaii implemented a program which include a $20 gift card for compliance with ADA-recommended strategies such as blood tests, eye exams and cholesterol tests, to prevent, treat, and manage diabetes or a $25 coupon for patients who go to the first session of smoking cessation, behavioral health counseling and diabetes education as appropriate.

Similarly, At Tufts Health Plan (THP), members are offered a $55 health rewards card upon completion of their annual PCP visit. The card allows the member to make health-related purchases. Tufts benefits from these visits with a primary care provider by declaring them a vital step in completing needed screenings and early detection of any chronic conditions.

Use Case: OPIOID use Control

The Opioid epidemic is a national crisis such that Federal legislation called The Comprehensive Addiction and Recovery Act (CARA) was recently passed. Statistically, 85% of addicts relapse into drugs within the year following treatment. Some treatment involves a requirement of face to face therapy. For instance, intensive inpatient therapy requires 28 hours of face-to-face therapy while intensive outpatient therapy requires 9 hours of face to face therapy per week. A prerequisite to maintain good status within these programs is strict adherence on the part of the addict. Noncompliance can result in dismissal from a drug therapy program.

In accordance with the present invention, patient visits to designated treatment facilities can be documented and verified. Further, in the case of face-to-face meetings, the invention contemplates event records being maintained for both or all parties participating in a treatment event. Event records for both a patient and a treatment professional can be accessed and compared to verify that both were at the same location. It is not always necessary that the location be specified as in the case of a face-to-face meeting the location can be arbitrary so long as both or all participants are in the same place.

The current invention allows the patients to prove compliance with these much sought after programs which often have waiting lists by documenting in the form of securely stored event records that the patent has attended the required meetings. Because the event records are under the patient's control, the patient may have fewer reservations about keeping the records. In many cases the patient will not even be required to submit event records so long as non-compliance is not suspected. The simple act of keeping the record will encourage patient compliance rendering more aggressive enforcement unnecessary. Used for this purpose, the invention promotes successful rehabilitative therapy outcomes, resulting in reduction of opioid use as well as less financial drain on the payers for subsequent and costly payments for an addict who relapses. Using the current invention to authenticate the user receiving the required care not only eliminates fraudulent reimbursement, it increases the likelihood of successful therapy by fulfilling therapeutic requirements creating less of a financial drain on the payer and society while curing the person of drug addiction.

Other Use Cases

While the current invention as authored addresses health care, it is not limited only to this industry. For instance, prescription compliance promotes better health outcomes. Biometric confirmation of being physically present to pick up the prescription is a straightforward use of the event record of the present invention. For example, patients who are willing to share their event records with pharmacies will have a strong disincentive to attempt filling prescriptions at multiple pharmacies as multiple visits to pharmacies in a short time period would be readily detected. Accordingly, patients willing to voluntarily share their event records related to pharmacy visits could be provided lower insurance rates, co-pays, deductibles or other incentives because they will cost the payers less.

As a second example, fraudsters (or the pharmacies themselves) commit fraud by filling falsified prescriptions in the names of non-existent patients, or real patients who have not yet picked up a prescriptions or real patients who do not pick up legitimate refills for one reason or another. The costs for this type of fraud, which is very similar to phantom billing fraud, eventually percolate down to the insured patients and taxpayers. Moreover, a patient may be prevented from filling a legitimate prescription for needed drugs because a pharmacy believes the prescription or refill has already been filled. The event records 115 of the present invention empower the patient to fight such abuse by documenting that they were not present at a pharmacy when a falsified prescription was filled.

Many payers offer wellness in the form of paid gym memberships or rewards for healthy activities such as walking, bicycling and the like. For instance, Humana has the "silver sneakers" program in which they pay for the gym memberships for senior citizens. The current invention allows the user to show they were physically present at the gym on occasions to show compliance and result in continued payments by Humana. Event records 115 also document various activities such as walking, hiking, running and the like. Because they incorporate both location and biometric information they are a more reliable record of activities than conventional records generated by fitness trackers. Moreover, because the present invention enables users to create and manage event records 115 under their own control, it is no longer necessary to attend a facility such as a gym as the event records can be maintained by the user without any facility.

Use Case: Financial Transactions

Many Credit Card companies have software to analyze potential fraudulent transactions. Often times a non-characteristic purchase will result in an immediate "fraud alert" phone call or text. The transaction is blocked until the card holder can confirm the transaction which is inconvenient and sometimes impossible.

The present invention allows merchants, banks and credit card companies the biometric confirmation that the user/purchaser is physically present at the location for the transaction. Conversely, the present invention may provide evidence that a particular user/purchaser was not present at the location for the transaction. This type of record keeping is simply not possible with prior techniques kept by automated systems or even manual tracking. For example, a user can establish permissions that allow a bank to query event records only when they have detected a potentially fraudulent transaction, and only for the time period of the transaction in concern. This user-permission control prevents the wholesale access to all event records and allows the user to specify how the user wants to respond to these requests. A user who is travelling may grant access to event records that evidence they are or have recently been located in New Mexico rather than their home. There may be no need to provide access to specific locations. When the bank fraud detection heuristics see a charge from a gas station in Gallup, N. Mex., rather than blocking the transaction and sending an alert to the user, they can send and access request to the user's mobile device, which can provide reliable information that the user (biometrically confirmed) is in New Mexico, and authorize the charge without obtrusive, inconvenient, or potentially dangerous consequences of blocking the transaction.

Visa recently announced that it would no longer require cardholder signatures for card present (point of sale) transactions. Card present transactions have always been given favored pricing because the risk of fraud was lower when the cardholder's signature appeared on the transaction record. However, the difficulty and expense of obtaining cardholder signatures outweighs the benefits to the cardholder. However, the risk of cardholder repudiation still exists even though the signature requirement has been found to be an inefficient solution.

In accordance with the present invention, user-controlled event records 115 provide a much simpler and more reliable evidence of card-present transactions as compared to signature requirements. Event records 115 record physical location information that evidences that a cardholder was at a particular location at the time of purchase, and biometric information that is in many cases better at uniquely identifying the cardholder than was a signature scrawled on a piece of paper or electronic input pad. Moreover, the cost of obtaining and maintaining the event record is not born by the merchant or credit card provider, and need not be examined in real time for each and every transaction. Credit card companies can, with a user's permission, spot check event records 115 to match Use Case: Telemedicine Telemedicine services are increasingly encouraged as a way to reduce the cost of health care services by enabling providers to interact with and diagnose certain classes of maladies over remote connections such as telephone and video conferencing. Telemedicine improves access to health care services for patients who are not near population centers where hospitals and health care providers tend to be more available. However, telemedicine presents analogous fraud issues, particularly phantom billing fraud, because it is more difficult to ensure that services associated with a reimbursement claim are have been provided without the implicit assurance of a patient's physical presence at a health care facility. Moreover, payers may require that health care providers be licensed in certain states and/or countries before they reimburse and conventional telemedicine services make this difficult to verify.

CMS (Center for Medicare Services) requires that in order for a provider to receive payment for a telemedicine service that the beneficiary (e.g., patient) is at an approved "originating site". Authorized originating sites include offices of a physician or practitioner, hospitals, community mental health centers and federally qualified health centers among others. The originating site is where the beneficiary is located when telemedicine services are provided. When telemedicine services are provided in this manner the location of the approved originating site can be used as the location information in event records 115 and can be captured and stored in user-controlled event records 115 using techniques described above. Additionally the present invention eliminates phantom billing fraud in conjunction with telemedicine services both at approved originating sites, and at other, more convenient and efficient sites.

In an implementation of the present invention, an event record 115 may include virtual location information that is analogous to the physical location information discussed with respect to medical services provided at a known location. Telemedicine sessions occur over network connections and those connections are identified in several ways that uniquely identify a particular communication session. For example, the software implementing a teleconference or video conference typically generates a session ID that uniquely identifies a particular connection and often maintains metrics of the connection such as duration of a call for billing and other purposes. This session ID can be exposed to the patient and recorded in the event record 115 as a virtual location information. Virtual location information may comprise any data that uniquely identifies the communication channel between participants in a telemedicine session as this data serves as a proxy for a fixed physical location used in more traditional face-to-face meetings. Alternatively or in addition, the health care provider can be given a session code to explicitly give the patient at the beginning and or end of a telemedicine session and that code is recorded in the patient's event record. As another alternative, since every computer and mobile device is already uniquely identified in a number of ways by globally unique identifiers (GUIDs) associated with the machine, the GUID of a health care provider's machine can be transmitted to the recipient's device and used as virtual location information. These types of virtual location information function in a manner similar to location information described above in that they, in combination with biometric information and other information maintained in the user-controlled event record 115, evidence that the user participated in a particular event such as telemedicine services. A payer entity, when granted permission by a user, can examine the event records corresponding to a request for reimbursement and verify that the telemedicine services were indeed provided.

Use Case: Remote Work Environments

Teleworking or "hoteling" is an increasingly common work environment because it provides efficient work environments and avoids wasteful employee costs of commuting and similarly wasteful employer costs of office space. Similar situations exist for many remote workers, particularly government workers such as police and fire and those who maintain distributed infrastructure. Adoption of these work practices is hampered not by actual compliance with the work requirements, but the need to evidence that employees or contractors were at the designated work location during the times they were working. Current technical solutions are intrusive and reduce work efficiency. For office work existing solutions may involve monitoring software required by the employer that requires periodically or randomly clicking on a dialog box control on a computer screen to confirm presence at that screen. These solutions have limited accuracy and are intrusive, defeating the efficiency possible with remote work.

The present invention enables the worker to maintain event records 115 that evidence when and where they are without intrusive check-in procedures. A personal audit trail is created without user effort. The worker controls access to the event records 115 and so is in control of obtrusive oversight while at the same time being enabled to provide evidence to third party services requesting evidence of their location when they are working.

Use Case: Frequent Flyers

In 1986, the U.S. federal government passed the Emergency Medical Treatment and Labor Act (EMTALA). This act requires any hospital that accepts payments from Medicare to provide care to any patient who arrives in its emergency department for treatment, regardless of the patient's citizenship, legal status in the United States or ability to pay for the services. EMTALA applies to ambulance and hospital care. As a result, many people use the emergency department as their primary care physician. This creates a financial drain on payers as well as taking needed resources from seriously injured and sick persons needing emergency care. These people are referred to as "frequent flyers" because they visit the ER so often. According to a study published in the Annals of Emergency Medicine, frequent flyers represent only 4.5% to 8% of all emergency patients, yet account for a disproportionately high percentage of all visits, between 21% and 28%.

Event records 115 can be valuable tools in efforts to divert ER patients from emergency rooms to more appropriate health care options. At the same time, the user control features of the present invention allow this diversion to continue to respect the user's/patient's own desires by allows the user to grant payers permission to be alerted when a "frequent flyer" presents for treatment in the emergency room. For example, when a patient's mobile device 100 contains event records 115 that indicate a location corresponding to a known location of an emergency room facility, the payer, or any other concerned management entity permitted by the user, can be alerted. When a patient activates a payer app on their mobile device 100 upon arriving at an ER the payer app may initially send current event record(s) 115 as permitted by the user. This is an example of using event record 115 to trigger some alert using processes in mobile device 100 to alert the remote service. Alternatively, when a patient first presents at an ER and checks in at the front desk with their insurance identification, the payer can be alerted and respond by sending a request for event records 115 to mobile device 100 associated with the patient/user who presented the insurance ID. In response, the payer can communicate with their member suggesting facilities close in proximity such as an urgent care center or physician's office. This reduces costs to the payer yet can provide the member more appropriate care as the member will be seen by a medical doctor at the urgent ca re center rather than a nurse at the ER.

I claim:

1. A user controlled mobile device for use by a health care recipient or health care worker which operates independent of health care facility hardware and for use in countering phantom billing fraud, the mobile device comprising:
   a sensor bank in the user controlled mobile device having one or more components for capturing and outputting location data and biometric data of the health care recipient and in certain instances the health care worker wherein one or more of the components for capturing and outputting biometric data are selected from the group consisting of fingerprint readers, image analyzers, voice processors, facial recognition scanners, iris scanners, or retinal scanners;

an event record creator in the user controlled mobile device creating an event record compiling without explicit user intervention the location data, the biometric data, and a timestamp corresponding to a time of capture of the location data and the biometric data occurring or detected at or near the time of the timestamp and controlled by the user evidencing an existence or an absence of phantom billing;

a permissions engine in the user controlled mobile device having an interface for receiving permissions indications from the health care recipient that grant access permissions and define access conditions to specific event records in the mobile device to third party services; and a data storage device in the user controlled mobile device storing the event record indicating when the health care recipient was at the particular location based upon the one or more confidence scores, the timestamp, the biometric data and location data evidences the location of the health care recipient at a time indicated by the timestamp and are accessible when the health care recipient-specified access permissions and access conditions are satisfied.

2. The user controlled mobile device of claim 1 further comprising a sensor fusion component implemented as part of a microprocessor, microcontroller or system-on-chip in the user controlled mobile device and configured to determine a composite confidence level to increase a confidence score of captured biometric data and/or captured location data.

3. The user controlled mobile device of claim 2, wherein the sensor bank comprises a first sensor for capturing biometric data and a second sensor for capturing the location data and wherein entries to the event record are entered only when the composite confidence level exceeds a predetermined threshold.

4. The user controlled mobile device of claim 1 wherein the sensor bank comprises a single sensor for capturing both the biometric data and the location data and wherein the biometric data and the location data generates a more reliable record under user control and independent of any facility records.

5. The user controlled mobile device of claim 1 wherein the sensor bank captures and outputs biometric data identifying the health care recipient.

6. The user controlled mobile device of claim 1 wherein the sensor bank captures and outputs location data for confirming the presence of the health care recipient at a time of a visit with a health care provider or for confirming the presence of the health care provider at the time of the visit with the health care recipient.

7. The user controlled mobile device of claim 1 wherein the user controlled mobile device is further configured to provide to a payer entity one or more responsive event records based upon successful authentication through a broker/interface that permissions have been granted for the one or more responsive event records.

8. The user controlled mobile device of claim 1 wherein the event record creator includes information identifying at least one property of the sensor bank that can be used to quantitatively or qualitatively determine a confidence score pertaining to the accuracy and/or trustworthiness of at least one of the biometric data and the location data.

9. The user controlled mobile device of claim 1 further comprising:

a message broker/interface receiving access request from a third party service, the access request containing credentials identifying the third party service and information about a particular event for which the third party service requires evidence that the health care recipient participated;

an access control module that receives the access request and evaluates from the information contained therein whether access to specified entries in the data storage device is permitted and when permitted retrieves stored access permissions from the data storage device;

wherein the message broker/interface receives results of the access control module and generates a message to the third party service indicating when a record that satisfies the access request does not exist in the data storage device, thereby evidencing that the particular event did not occur.

10. A user controlled mobile device creating a personal audit trail for use by a health care recipient, a health care worker or a health care employer, the user controlled mobile device which operates independent of health care facility hardware and for use in countering phantom billing fraud in connection with receiving or providing health care services comprising:

one or more components capturing and outputting biometric data and one or more components capturing and outputting location data wherein the one or more components capturing and outputting biometric data are selected from the group consisting of fingerprint readers, image analyzers, voice processors, facial recognition scanners, iris scanners, or retinal scanners;

a processor configured to receive the biometric data and the location data and determine a confidence score; and a data storage device in the mobile device holding an event record created without explicit user intervention indicating whether the particular user was at the particular location, the event record comprising the confidence score, a timestamp corresponding to events at or near a time of the timestamp including a time of capture of the biometric data and the location data, the biometric data and the location data, whereby the stored event record serves as the personal audit trail evidencing whereabouts of the particular user at a time indicated by the timestamp and further evidencing an existence or an absence of phantom billing.

11. The user controlled mobile device of claim 10 wherein the sensor bank comprises a first sensor for capturing biometric data and a second sensor for capturing the location data.

12. The user controlled mobile device of claim 10 wherein the sensor bank comprises a single sensor for capturing both the biometric data and the location data.

13. The user controlled mobile device of claim 10 wherein the sensor bank comprises a plurality of sensors for capturing and outputting biometric data and the mobile device further comprises a sensor fusion component receiving the biometric data from the plurality of sensors and generating the confidence score based on a quantitative and qualitative combination of individual confidence scores of each of the plurality of biometric sensors to determine the composite confidence level to improve the accuracy and reliability of the captured biometric data.

14. The user controlled mobile device of claim 10 wherein the sensor bank comprises a plurality of sensors for capturing and outputting location data and the mobile device further comprises a sensor fusion component receiving the location data from the plurality of sensors and generating the confidence score based on a quantitative and qualitative combination of individual confidence scores of each of the plurality of location sensors to determine a composite confidence level to determine the composite confidence level to increase the confidence score of the captured location data.

15. The user controlled mobile device of claim 10 further comprising a permissions manager in the user controlled mobile device configured to receive the third party requests for event records and evaluate the third party requests against access requirements specified by the particular user.

16. The user controlled mobile device of claim 11 further comprising a permissions engine having an interface for receiving permissions indications from the particular user that grant access permissions and conditions to specific entries in the data storage device to third party services specified by the particular user, wherein the access permissions and conditions are stored with each entry in the data storage.

17. The user controlled mobile device of claim 10 further comprising an access control module that receives requests for access to specified entries in the data storage device, retrieves stored access permissions from the data storage device, evaluates the request to determine when the access permissions have been satisfied, and decrypts the specified entries.

18. The user controlled mobile device of claim 10 wherein the processor determines the composite confidence level algorithmically based on a confidence level of the biometric data or a confidence level of the location information.

19. The user controlled mobile device of claim 10, wherein the stored event record evidences that the health care worker as employee or contractor was at a designated patient location during times they were working.

20. The user controlled mobile device of claim 10, where the event record for both a patient and a treatment professional can be accessed and compared to verify that both were at the same location.

21. A mobile device for use by and controlled by a user in countering phantom billing fraud in connection with receiving telemedicine services or providing telework services, the device comprising:

one or more components capturing and outputting biometric data identifying the user, wherein the one or more components capturing and outputting biometric data are selected from the group consisting of fingerprint readers, image analyzers, voice processors, facial recognition scanners, iris scanners, or retinal scanners;

one or more components in the mobile device capturing and outputting virtual location data identifying a communication channel used by the user to receive the telemedicine services or provide the telework services;

an event record creator to create an event record in the mobile device compiling without explicit user intervention the virtual location data, the biometric data, and a timestamp corresponding to a time of capture of the virtual location data and the biometric data occurring or detected at or near the time of the timestamp;

and a data storage device in the mobile device storing the event record and, whereby the stored event record evidences that the user received the telemedicine services or provided telework services at a particular time indicated by the timestamp and are accessible when user-specified access permissions and access conditions are satisfied.

22. The mobile device of claim 21 further comprising:

a message broker/interface for receiving requests for event records from third party services; and a permissions engine having an interface for receiving permissions indications from and under control by the health care recipient that grant access permissions and define access conditions to specific event records to third party services specified by the particular user;

wherein the permissions engine is coupled to receive the third party requests for event records and evaluate the third party requests against the access requirements specified by the health care recipient, wherein the message interface responds to the requests for event records with information about the existence of event records that satisfy the request when the health care recipient-specified access requirements are satisfied and wherein the event record evidences an absence of phantom billing.

* * * * *